United States Patent
Shi et al.

(10) Patent No.: US 10,280,444 B2
(45) Date of Patent: May 7, 2019

(54) METHOD OF QUANTITATING SORPTION OF STANNOUS BY MICROBIAL CELLS OF A BIOFILM

(71) Applicant: The Procter & Gamble Company, Cincinnati, OH (US)

(72) Inventors: Yunming Shi, Beijing (CN); Ross Strand, Singapore (SG); Jinlan Chang, Beijing (CN); Tao He, Loveland, OH (US); Donald James White, Jr., Fairfield, OH (US); Yanyan He, Beijing (CN); Matthew Lloyd Barker, Mason, OH (US); Weili Dong, Wuhan (CN)

(73) Assignee: THE PROCTER & GAMBLE COMPANY, Cincinnati, OH (US)

( * ) Notice: Subject to any disclaimer, the term of this patent is extended or adjusted under 35 U.S.C. 154(b) by 0 days.

(21) Appl. No.: 15/260,344

(22) Filed: Sep. 9, 2016

(65) Prior Publication Data

US 2017/0056531 A1    Mar. 2, 2017

(51) Int. Cl.
| | |
|---|---|
| C12Q 1/02 | (2006.01) |
| C12Q 1/689 | (2018.01) |
| G01N 21/64 | (2006.01) |
| A61B 5/00 | (2006.01) |

(52) U.S. Cl.
CPC .............. *C12Q 1/025* (2013.01); *C12Q 1/689* (2013.01); *G01N 21/6428* (2013.01); *G01N 21/6458* (2013.01); *A61B 5/0071* (2013.01); *A61B 5/0088* (2013.01); *G01N 2021/6441* (2013.01)

(58) Field of Classification Search
None
See application file for complete search history.

(56) References Cited

U.S. PATENT DOCUMENTS

| | | | |
|---|---|---|---|
| 6,309,835 B1 * | 10/2001 | Iyer | C12Q 1/04 424/49 |
| 9,042,967 B2 | 5/2015 | Dacosta et al. | |
| 9,310,353 B2 | 4/2016 | Haught et al. | |
| 2006/0275847 A1 | 12/2006 | Goodyer et al. | |
| 2015/0241409 A1 | 8/2015 | Haught et al. | |

FOREIGN PATENT DOCUMENTS

WO    WO 2015/139577 A1 *    9/2015

OTHER PUBLICATIONS

Lan H. et al. Fluorescence Turn-On Detection of Sn2+ in Live Eukaryotic and Prokaryotic Cells. Analyst 139(20)5223-5229, 2014. (Year: 2014).*
Otten M. et al. Acute and Substantive Action of Antimicrobial Toothpastes and Mouthrinses on Oral Biofilm In vitro. European J of Oral Sciences 119(2)151-155, 2011. (Year: 2011).*
Ellingsen Jan Eirik et al., Treatment of dentin with stannous fluoride—SEM and electron microprobe study Scand J. Den Res, Aug. 31, 1987; No. 4, vol. 95, pp. 281-286.
International Search Report for AA1033 (PCT/CN2015/089238 dated Sep. 9, 2015.
Lan, Haichuang et al., Fluorescence turn-on detection of Sn2+ in live eukaryotic and prokaryotic cells, Analyst, Jul. 21, 2014, No. 20, vol. 139, pp. 5223-5229.
Madrakian, Tayyebeh et al., "Simultaneous spectrophotometric determination of Sn(II) and Sn(IV) by mean centering of ratio kinetic profiles and partial least squares methods", Feb. 21, 2007, No. 5, vol. 72, pp. 1847-1852.
PCT International Search Report, dated Dec. 6, 2017, 12 pages.

* cited by examiner

*Primary Examiner* — Ralph J Gitomer
(74) *Attorney, Agent, or Firm* — James E. Oehlenschlager (57) ABSTRACT

A method of quantitating sorption of stannous by microbial cells of a biofilm is an effective way of assessing efficacy of oral care products containing stannous.

10 Claims, 6 Drawing Sheets

METHOD OF QUANTITATING SORPTION OF STANNOUS BY MICROBIAL CELLS OF A BIOFILM

FIELD OF THE INVENTION

The present disclosure is directed to methods for assessing stannous containing oral care products.

BACKGROUND OF THE INVENTION

Methods for quantitating the efficacy of oral care products (e.g., toothpaste, mouthwash etc.) at dislodging cells from biofilm test surfaces or inhibiting or delaying the accumulation of cells on a test surface have generally been described. Also, fluorescent probes, and confocal laser scanning microscopy (CLSM), have been generally used to assess bacterial vitality of biofilm. Stannous ($Sn^{2+}$) has been added to oral care products to prevent dental plaque and oral disease. $Sn^{2+}$ is found to effectively inhibit certain bacteria that can lead to tooth decay in human interproximal dental plaque. However, there is a need for a specific method at quantitating the efficiency of stannous containing oral care products, and its bacteriostatic or bactericidal efficacy against biofilm.

SUMMARY OF THE INVENTION

The present invention addresses at least one of these needs by providing a method of quantitating sorption of stannous by microbial cells of a biofilm comprising the steps: treating the biofilm with a stannous containing oral care product; labeling the biofilm with a microbial fluorescent probe; labeling the biofilm with a stannous fluorescent probe; and quantitating the labeled cells by measuring fluorescence light emitted from the labeled cells by, for example, confocal laser scanning microscopy. Another aspect of the invention provides a kit comprising a microbial fluorescent probe; a stannous fluorescent probe; and optionally use-instructions.

The present invention is based, in part, upon the surprising discovery that certain stannous probes can be used in quantitating sorption of stannous by microbial cells of biofilm.

One advantage of the present method is that the stannous and microbial probes fluoresce at different colors and as such co-localization of the probes in bacteria of biofilm can be determined.

Another advantage of the present invention is the methods can be used to identify more efficacious oral care compositions as these compositions relate to stannous delivery and/or efficacy in biofilm.

Yet another advantage of the present invention is the methods can be used to demonstrate to consumers and dental professionals how stannous containing oral products work as these products relate to stannous delivery and/or efficacy in biofilm.

These and other features, aspects and advantages of specific embodiments will become evident to those skilled in the art from a reading of the present disclosure.

BRIEF DESCRIPTION OF THE DRAWINGS

The embodiments set forth in the drawings are illustrative in nature and not intended to limit the invention defined by the claims. The following detailed description of the illustrative embodiments can be understood when read in conjunction with the following drawings, where like structure is indicated with like reference numerals and in which:

DETAILED DESCRIPTION OF THE INVENTION

The following text sets forth a broad description of numerous different embodiments of the present disclosure. The description is to be construed as exemplary only and does not describe every possible embodiment since describing every possible embodiment would be impractical, if not impossible. It will be understood that any feature, characteristic, component, composition, ingredient, product, step or methodology described herein can be deleted, combined with or substituted for, in whole or part, any other feature, characteristic, component, composition, ingredient, product, step or methodology described herein. Numerous alternative embodiments could be implemented, using either current technology or technology developed after the filing date of this patent, which would still fall within the scope of the claims.

One aspect of the present disclosure is directed to method of quantitating sorption of stannous by microbial cells of a biofilm comprising the steps: treating the biofilm with a stannous containing oral care product; labeling the biofilm with a microbial fluorescent probe; labeling the biofilm with a stannous fluorescent probe; and quantitating the labeled cells by measuring fluorescence light emitted from the labeled cells by confocal laser scanning microscopy (CLSM). These steps need not be conducted in any specific order.

Treating the Biofilm with a Stannous Containing Oral Care Product

The term "biofilm" refers to the layer(s) of cells attached to a surface. A biofilm can include both alive and growing microbe cells as well as dead microbe cells. The biofilm can be composed of one cell type or it may be composed of two or more cell types, such as for example, a biofilm complex that is a multispecies bacterial community. A specific type of biofilm is plaque biofilm (i.e., biofilm that typically forms on tooth surfaces in the human mouth). Bacteria in a plaque biofilm have significantly different physiological characteristics, e.g. increased resistance to detergents and antibiotics, making biofilm research highly important. A non-limiting list of oral bacterial species is described at U.S. Pat. No. 6,309,835 B1, column 7, lines 12-30. The biofilm may be either in vitro biofilm or in situ biofilm. Preferably the biofilm is in situ plaque biofilm because it more accurately reflects the conditions of the human mouth by providing a natural and undistributed biofilm. One approach that lends itself well to assessing stannous retention in the biofilm over a defined period of time is using in situ plaque biofilm.

Figure 2:
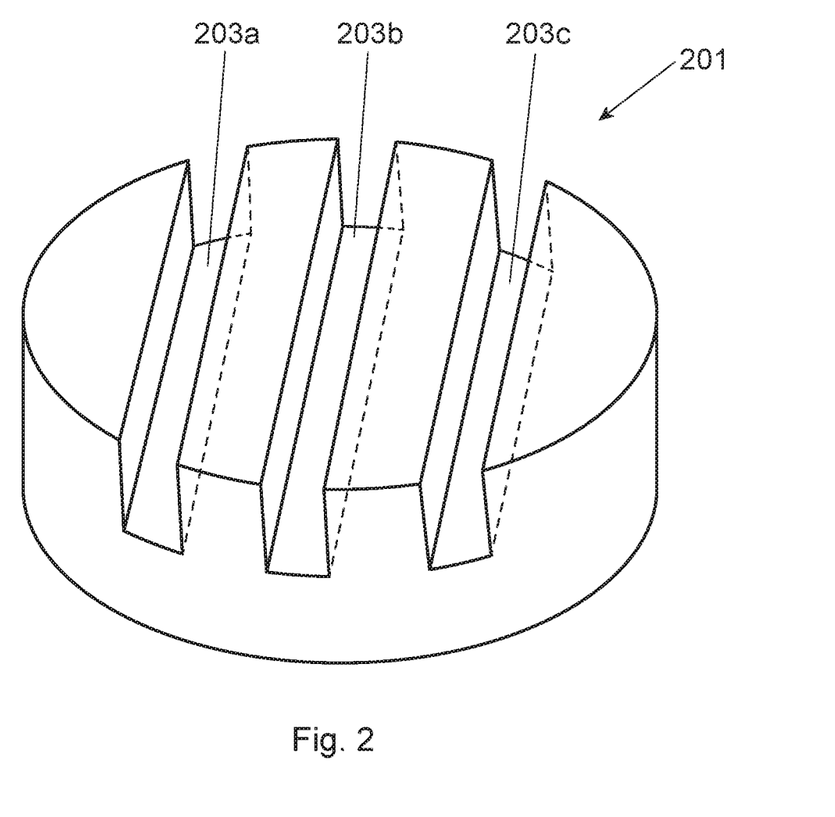
FIG. 2 is a perspective view of the hydroxyapatite disk having grooves therein.
Figure 3:
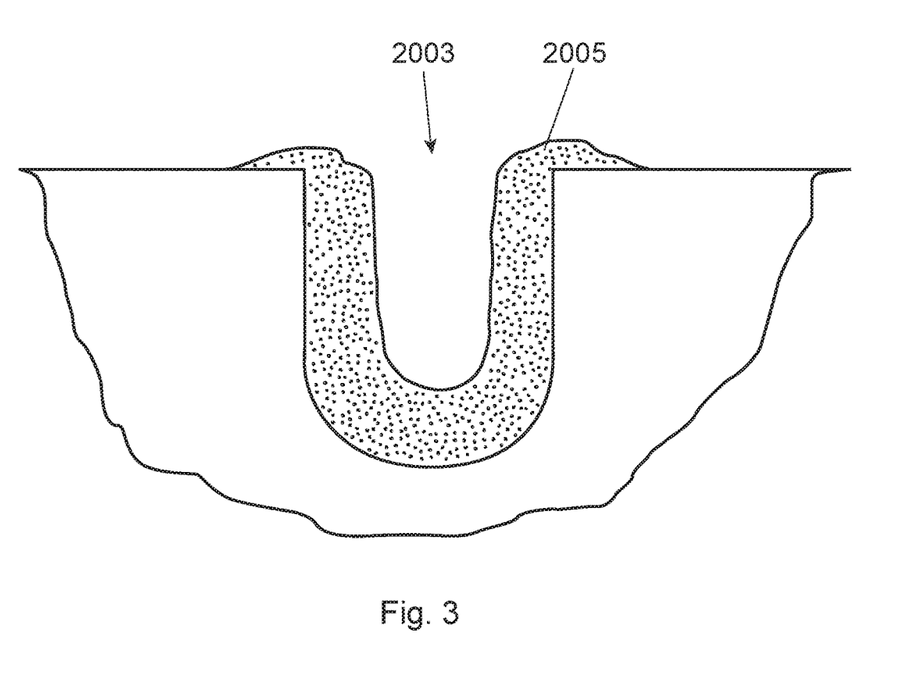
FIG. 3 is a schematic of a cross sectional view of the groove with biofilm therein.

A number of different surfaces for which the biofilm may attach are contemplated. These surfaces may include, for example, human enamel, bovine enamel, bovine dentine, hydroxyapatite, polished glass, and titanium. Considering the roughness of the surface of the substrate and its free energy are important factors for the in situ growth of plaque biofilm, enamel or hydroxyapatite are preferred surfaces to mimic a natural substrate for growth of plaque biofilm. On the other hand, due to the known auto-fluorescence of enamel, hydroxyapatite is more preferred for the in situ growth of plaque biofilm. Hydroxyapatite, also called hydroxylapatite, ("HA") is a mineral form of calcium apatite generally having the formula $Ca_{10}(PO_4)_6(OH)_2$. In particularly preferred approach, HA containing pieces (e.g., small disks) are used. These HA pieces are relatively small, preferably having an overall volume of 7 $mm^3$ to 110 $mm^3$, preferably from 25 $mm^3$ to 35 $mm^3$. The HA pieces are designed having a plurality of grooves (to allow plaque biofilm to attach inside the groove). For clarification, either in situ or in vitro plaque biofilm may be used to attach to the inside of the groove(s), but in situ plaque biofilm is preferred. The plurality of grooves preferably have dimensions that are from 50 um to 500 um deep and from 50 um to 500 um wide, more preferably from 100 um to 400 um deep and from 100 um to 400 um wide, even more preferably at least one of the grooves is from 250 um to 350 um deep and from 250 um to 350 um wide. Without wishing to be bound by theory, many human subjects do not care to have an oral appliance (containing these HA pieces) for more than two to three days. With grooves smaller than these dimensions, the groove is filled up with in situ plaque biofilm thereby not allowing the subject oral care product and/or fluorescent probes to penetrate into the groove. On the other hand, if the dimensions of the groove are too large then the grooves do not lend themselves well to biofilm growth or attachment, particularly if the human subject is only going to wear the oral appliance for two to three days. In addition, these preferred groove dimensions provide for an optimum cross section view by conventional CLSM. In a specific example, and turning to FIG. 2, the HA disk (201) has three parallel grooves (203) (the two sides' grooves (203a and 203c) are 300 um wide and 300 um deep; while the middle grove (203b) (in between the two side grooves) is 500 um wide and 500 um deep). The middle groove is designed wider and deeper than the two sides' grooves so that the HA disk can be more easily separated into two identical half-disks for head-to-head comparison purposes. FIG. 3 is a schematic of a cross sectional view of the groove (2003) with biofilm (2005) therein.

Figure 1:
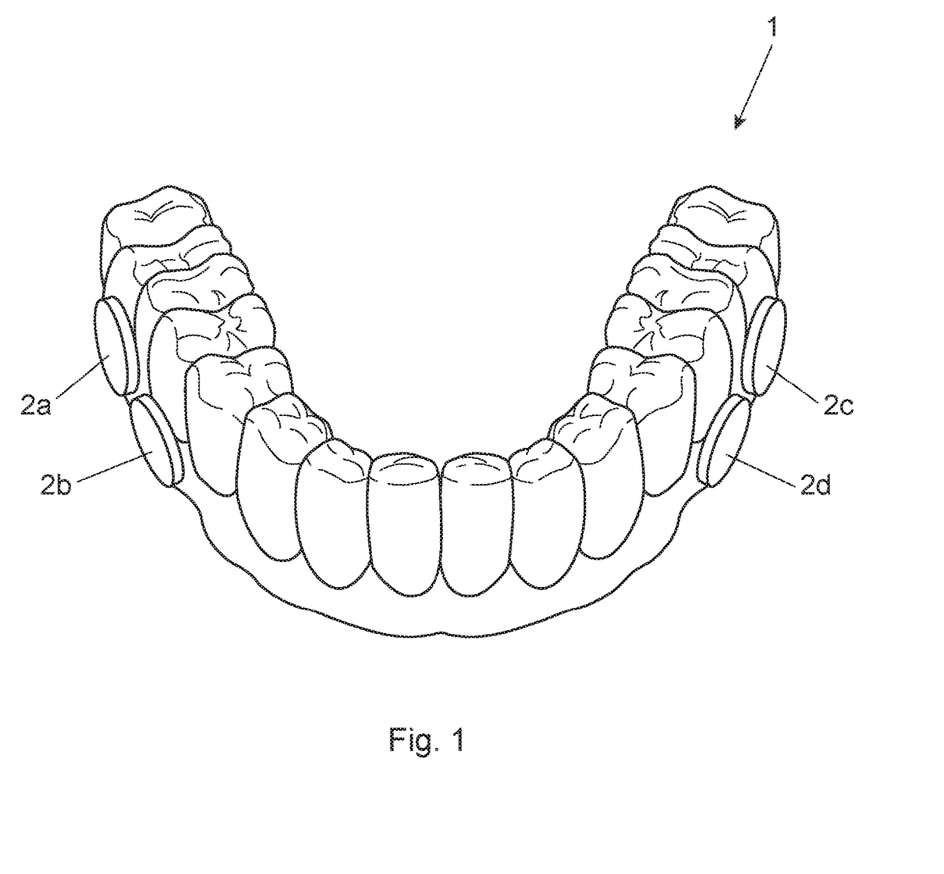
FIG. 1 is a perspective view of an oral splint with hydroxyapatite disks attached thereto.

Preferably the in situ plaque biofilm is attached to the surface of a HA pieces as a result of the HA pieces being attached to an oral appliance (e.g., oral split or mouthpiece) worn by human subjects for a defined period of time. This defined period of time is preferably from 6 hours to 4 days, more preferably from 1 day to 3 days, alternatively about 2 days. Accordingly, the method may comprise the step of having human subjects wearing the oral appliance for 6 hours to 4 days, preferably 1-3 days, more preferably 2 days; wherein at least a portion of the oral appliance comprises HA as a surface of the biofilm, and wherein the biofilm is an in situ plaque biofilm. The term "oral appliance" means a device that can be temporarily worn inside the oral cavity (i.e., mouth) of a human subject for up to multiple days at a time (but temporarily removed during eating or oral hygiene and the like). Non-limiting examples of an oral appliance include an oral split, mouthpiece, and retainer. The oral appliance preferably has a plurality of HA containing pieces (e.g., small disks) releasably attached thereto. In other words, the human subject wears the oral appliance as to allow biofilm to attach/grow to the surfaces and grooves of the HA disk. After 6 hours to 4 days, preferably 2-3 days, more preferably 2 days, the HA disks are removed by the oral appliance that was worn by the human subject. FIG. 1 is an example of a splint (1) having a plurality of HA disks (2a, 2b, 2c, 2d, 2e) releasably attached to the splint. The splint (1) is worn over the teeth of a human subject (not shown) for a defined period of time with the objective of having biofilm grow/attach to the HA disks, preferably in grooves of the HA disks. In FIG. 1, the plurality of HA disks are on the interdental lingual side of the oral applicant. Although not shown in FIG. 1, a preferred location of the HA pieces is on the buccal side of the appliance. Without wishing to be bound by theory, the buccal side is even more difficult to brush thereby providing in situ plaque biofilm that is likely thicker (i.e., grows or forms more quickly than from other locations in the oral cavity). Moreover, there is also a suggestion that the in situ plaque biofilm resulting from the buccal side maybe by more toxic or pathogenic.

The biofilm may be treated with the stannous containing oral care product either in vivo or ex vivo. "In vivo" means that which takes place within the organism, specifically within the oral cavity of the human subject. For example, the human subject may wear an oral splint (and the HA disks releasably attached thereto) while using the stannous containing oral care product. "Ex vivo" means that which takes place outside an organism, specifically outside the oral cavity of the human subject. For example, after the splint is worn, the HA disks may be removed and then treated with the subject stannous containing oral care product. Such an ex vivo approach is preferable when assessing the penetration of stannous in the biofilm or the amount of the stannous deposition in the biofilm (e.g., single or multiple stannous containing product usage).

The stannous containing oral care product may be any product that is designed to be primarily used for oral hygiene in humans. Such stannous containing oral care products may include dentifrice, toothpaste, mouthwash etc. The oral care products of the subject invention are those containing stannous ($Sn^{2+}$). A non-limiting example of a stannous ingredient used in stannous containing oral care products includes stannous fluoride. Such oral care products may typically contain from 0.0025% to 2%, by weight of the composition, of stannous fluoride.

In an alternative embodiment, the biofilm attaches to a test piece of mammalian (e.g., human or bovine) enamel surface. That is, pieces of enamel are subject to a relatively longer term study (e.g., 5-21 days). These pieces can also be releasably attached to an oral care appliance and worn by a human subject. This in situ method can used to measure stannous delivery and/or penetration and/or the effect of an oral care composition to stannous bioavailability.

Labeling the Biofilm with a Microbial Fluorescent Probe

The biofilm is labeled with a microbial fluorescent probe. "Microbial fluorescent probe" means a fluorescent probe that binds to microbes of a biofilm. One class such probes includes fluorescently labeled oligonucleotides, preferably rRNA-directed oligonucleotides. Non-limiting examples include SYTO™ branded dyes. One specific example is SYTO-9, wherein excitation is a 485 (DNA) and 486 (RNA), and light emission is detected at 498 (DNA) and 501 (RNA). Within this class of rRNA-directed oligonucleotides dyes, a sub-class of dyes may be used to distinguish between dead or alive microbes. Another class of microbial fluorescent probes include extracellular polymer substances (EPS)- specific fluorescent stains or lectins. A commercially available example of a microbial fluorescent probe is LIVE/DEAD® BacLight™ fluorescence assay stains. See also U.S. Pat. No. 6,309,835 B1, at column 8, Table 1. These microbial fluorescent probes are widely available as well as the procedure details in how to use them to quantitatively determine the amount of microbes as well as quantitatively determine what portion of these microbes are alive or dead.

Labeling the Biofilm with a Stannous Fluorescent Probe

The biofilm is labeled with a stannous fluorescent probe. Examples of a stannous fluorescent probe suitable for labeling the biofilm may any one following of the compounds: (a) tert-butyl (3',6'-diamino-3-oxospiro[isoindoline-1,9'-xanthen]-2-yl)carbamate; (b) tert-butyl (3',6'-bis(dimethylamino)-3-oxospiro[isoindoline-1,9'-xanthen]-2-yl)carbamate; (c) tert-butyl (3',6'-bis(diethylamino)-3-oxospiro[isoindoline-1,9'-xanthen]-2-yl)carbamate; (d) tert-butyl (3',6'-bis(ethylamino)-2',7'-dimethyl-3-oxospiro[isoindoline-1,9'-xanthen]-2-yl)carbamate; (e) tert-butyl (3',6'-diamino-2',7'-dimethyl-3-oxospiro[isoindoline-1,9'-xanthen]-2-yl)carbamate; (f) tert-butyl (3-oxo-3',6'-di(pyrrolidin-1-yl)spiro[isoindoline-1,9'-xanthen]-2-yl)carbamate; (g) tert-butyl (3-oxo-3',6'-bis(phenylamino)spiro[isoindoline-1,9'-xanthen]-2-yl)carbamate; (h) tert-butyl (3-oxo-3',6'-di(piperidin-1-yl)spiro[isoindoline-1,9'-xanthen]-2-yl) carbamate; (i) tert-butyl (3',6'-dimorpholino-3-oxospiro[isoindoline-1,9'-xanthen]-2-yl)carbamate; (j) tert-butyl(2',7'-dibutyl-3', 6'-bis(diethylamino)-3-oxospiro[isoindoline-1, 9'-xanthen]-2-yl)carbamate; (k) tert-butyl (2',7'-dimethyl-3-oxo-3', 6'-di(piperidin-1-yl)spiro[isoindoline-1,9'-xanthen]-2-yl)carbamate; (l) tert-butyl (3-oxo-1',2',3',4',10',11',12', 13'-octahydrospiro[isoindoline-1,7'-pyrano[2,3-f:6,5-f'] diquinolin]-2-yl)carbamate; tert-butyl (3-oxo-1',2',3',4',8',9', 10',11'-octahydrospiro[isoindoline-1,6'-pyrano[3,2-g:5,6-g'] diquinolin]-2-yl)carbamate; (n) N-(3',6'-bis(diethylamino)-3-oxospiro[isoindoline-1,9'-xanthen]-2-yl)propionamide; (p) N-(3',6'-bis(diethylamino)-3-oxospiro[isoindoline-1,9'-xanthen]-2-yl)butyramide; and (q) N-(3',6'-bis(diethylamino)-3-oxospiro[isoindoline-1,9'-xanthen]-2-yl)pentanamide. Preferably the stannous probe is selected from: N-(3', 6'-bis(diethylamino)-3-oxospiro[isoindoline-1,9'-xanthen]-2-yl)propionamide; N-(3',6'-bis(diethylamino)-3-oxo spiro [isoindoline-1,9'-xanthen]-2-yl)butyramide; and N-(3',6'-bis (diethylamino)-3-oxospiro[isoindoline-1,9'-xanthen]-2-yl) pentanamide. Generally these stannous fluorescent probes contain a Rhodamine B derivative moiety as fluorophore, linked via amide moiety to a carbazate group. Further details are described in the WO or US publications of patent application number PCT/CN2015/074142, with the international filing date of Mar. 13, 2015, (P&G Case No. AA916M, "STANNOUS FLUORESENT PROBE"). One or more of these probes may be available from Dr. Tao Yi, of Fudan University, Shanghai, China.

The subject biofilm is incubated with the stannous probe in dark for 15-60 minutes, preferably 30 minutes and excitation light is provided to the incubated biofilm at a wavelength from at least from 520 nm to 580 nm, alternatively at 560 nm. Light emission is detected from the stannous probe at a wavelength from at least 560 nm to 660 nm. The procedure details in how to use stannous probes to quantitatively determine are in the above-identified patent publication and can also be analogized to widely available literature associated with Rhodamine B-based fluorescent probes generally.

Quantitating the Labeled Cells by Measuring Fluorescence Light Emitted from the Labeled Cells The method of the present invention comprising the step of quantitating the labeled cells by measuring fluorescence light emitted from the labeled cells. One preferred instrument in performing such quantification is confocal laser scanning microscopy (CLSM). Commercially available software is able to quantity pixels from the images taken of the fluorescent. Three dimensional images can be constructed from a number of single images taken of the labeled cells.

Examples

Data is provided on the co-localization percentage of stannous in bacteria (of biofilm) for several stannous containing toothpastes and a negative control. Data is also provided on the overlap coefficient of stannous containing toothpaste on biofilm over time. Methodology is first described.

The substrate for biofilm growth is described. Hydroxyapatite disks are used for in situ growth of biofilm. The HA disks are designed having three parallel grooves (200 um wide, 200 um deep for two sides' grooves, while 500 um wide, 500 um deep for the middle groove) in each disk. When attaching disks to subject's mouth, keeping these grooves vertical, to mimic interproximal gap between teeth, the hard-to-clean area where plaque accumulates. This model allows the collection of undisturbed plaque from the grooves. HA disks are manufactured by Shanghai Bei'erkang biomedicine limited company.

Human subjects wearing a splint are described. Each subject wears up to 12 HA disks on the splint to make sure 9 HAP disks are available after 48 hours. A non-limiting example of such a splint and HA disks are shown in FIG. 1. The device (1) holds a plurality of HA disks (2a-2d). Although not shown in FIG. 1, the disks can be positioned such that the recede in the inter-dental space between the teeth (since this location is prone to plaque (given the difficulty in cleaning etc.)). The subjects withdraw the splint only during meals (the splint stored in an opaque container in humid conditions) and to perform oral hygiene procedures. Immediately thereafter, the splint is worn again. Subjects are asked to use a straw when drinking.

The procedure for in situ biofilm release from HA disk is described. All HA disks are removed from the splint at 48 hours by tweezers. Tweezers are used to hold the edge of HA chips and transfer the HA disk to a 2 mL centrifuge tube containing PBS (phosphate buffered saline) solution. Tweezers are washed thoroughly (water; 75% alcohol; and then deionized water) before every disk transfer.

The preparation for toothpaste supernatant is described. 15 grams of deionized water is added to 5 grams toothpaste. After stirring thoroughly, the mixture is centrifuge 12,000 rotations per minute for 20 minutes. The supernatant is prepared one day before usage and stored at 4° C.

After the HA disks are removed from the splint, The HA disks are used for ex vivo treatment by different oral care products. After being treated with the subject supernatant and labeled with microbial fluorescent probe and stannous fluorescent probe, the biofilm in the grooves is measured by confocal laser scanning microscopy (CLSM).

Disk preparation is described. The HA disks are rinsed in PBS solution and each HA disk is divided into two halves by tweezers. Thereafter each half-disk is placed into 500-1000 ul of PBS solution statically for 1 minute. Each disk is treated for two minutes by either PBS solution or toothpaste supernatant. Each disk is washed by holding each disk with tweezers, shaken for ten rounds of back and forth in 1 ml of PBS solution, and then this washing cycle is repeated. Then each disk is immersed into 500-1000 ul PBS solution statically for 5 minutes.

Fluorescence staining and microscopy is described. It is reported that the LIVE/DEAD® BacLight™ system is a reliable alternative when assessing bacterial vitality in a natural plaque biofilm, in which there are several types of bacteria present. The LIVE/DEAD® BacLight™ fluorescence assay stains the bacteria in red or green depending on the permeability of their membrane. The ratio of green/red is well correlated with live/dead ratio. It is considered that live/dead staining methods are reliable when analyzing antimicrobial agent activity. After treatment and immersing, each half-disk is stained with the Sn probe together with Syto-9 probe (containing 5 uM Syto-9+5 uM Sn probe) for 30 minutes in the dark and the other half-disk is stained with L7012 LIVE/DEAD® dye solution (containing 5 uM Syto-9+30 uM propidium iodide) for 15 minutes in the dark. After staining, each disk is immersed into 500-1000 ul PBS solution statically for 2 minutes. The disks are washed again, by holding each disk with tweezers, shaken for five rounds of back and forth in 1 ml PBS solution, and repeated. For L7012 LIVE/DEAD® dye stained samples, the following parameters are used: λex=488 nm, λem=500/635 nm, 20× objective lens, and scanning from bottom of surface bacteria for 60 um with step size=3 um. For SYTO-9/Sn dye stained samples, the following parameters are used: λex=488 nm/543 nm, λem=500/580 nm, 20× objective lens, and scanning from bottom of surface bacteria for 60 um with step size=3 um.

Confocal Laser Scanning Microscopy (CLSM) is described. The Leica™ TCS SP8 AOBS spectral confocal microscope is used. The confocal system consists of a Leica™ DM6000B upright microscope and a Leica™ DMIRE2 inverted microscope is used. An upright stand is used for applications involving slide-mounted specimens; whereas the inverted stand, having a 37° C. incubation chamber and $CO_2$ enrichment accessories, provides for live cell applications. The microscopes share an exchangeable laser scan head and, in addition to their own electromotor-driven stages, a galvanometer-driven high precision Z-stage which facilitates rapid imaging in the focal (Z) plane. In addition to epifluorescence, the microscopes support a variety of transmitted light contrast methods including bright field, polarizing light and differential interference contrast, and are equipped with 5×, 20×, 40×, 63× (oil and dry) and 100× (oil) Leica™ objective lenses.

The laser scanning and detection system is described. The TCS SP2 AOBS confocal system is supplied with four lasers (one diode, one argon, and two helium neon lasers) thus allowing excitation of a broad range of fluorochromes within the UV, visible and far red ranges of the electromagnetic spectrum. The design of the laser scan head, which incorporates acousto-optical tunable filters (AOTF), an acousto-optical beam splitter (AOBS) and four prism spectrophotometer detectors, permits simultaneous excitation and detection of three fluorochromes. The upright microscope also has a transmission light detector making it possible to overlay a transmitted light image upon a fluorescence recording.

Leica™ Confocal software is used. The confocal is controlled via a standard Pentium PC equipped with dual monitors and running Leica™ Confocal Software. The Leica Confocal Software provides an interface for multi-dimensional image series acquisition, processing and analysis, that includes 3D reconstruction and measurement, physiological recording and analysis, time-lapse, fluorochrome co-localization, photo-bleaching techniques such as FRAP and FRET, spectral immixing and multicolour restoration. Regarding image analysis, the L7012 LIVE/DEAD® dye stained samples, are chosen to quantify ratio of red and green pixels, and for SYTO-9/Sn dye stained samples are chosen to quantify overlap efficiency of red and green pixels.

Figure 4:
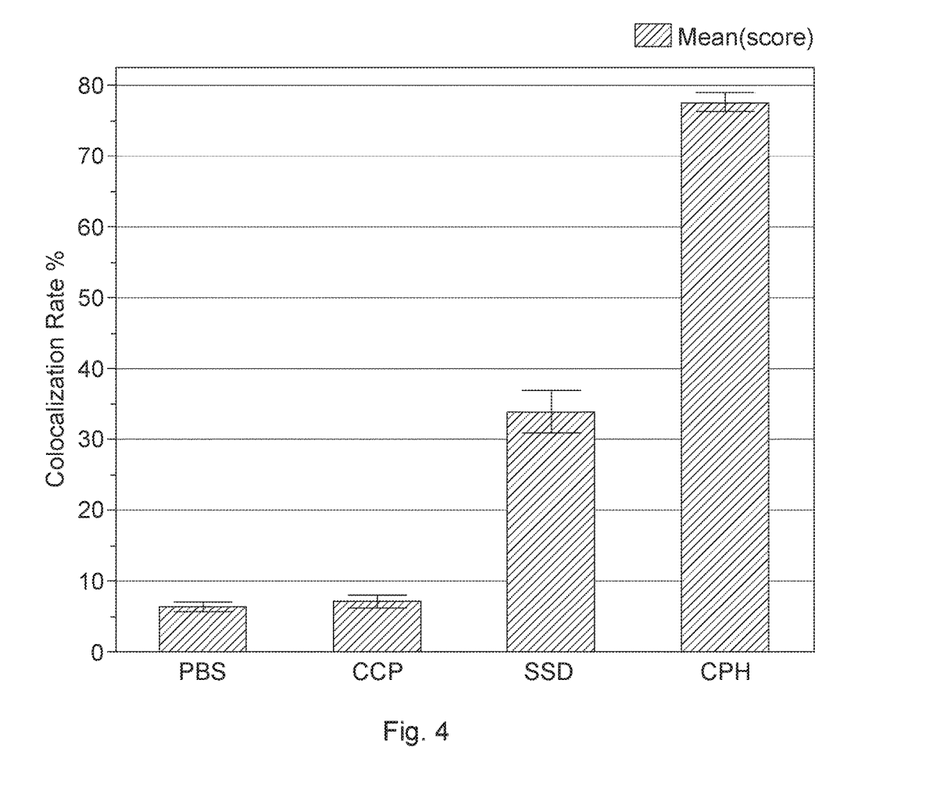
FIG. 4 is a bar graph providing a co-localization percentage of stannous in bacteria (of biofilm) for several stannous containing toothpastes and a negative control.
Figure 5:
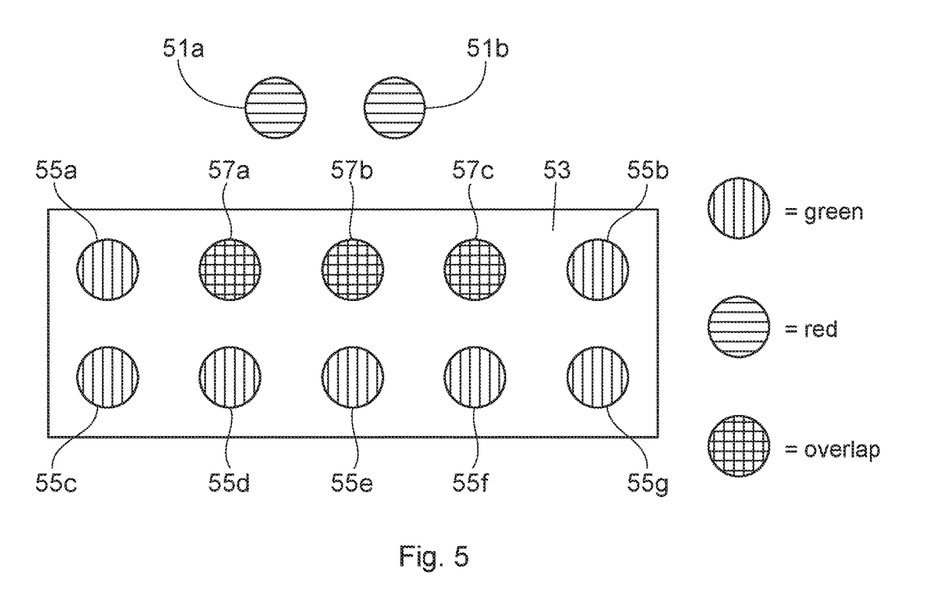
FIG. 5 is a schematic example of how the co-localization percentage of stannous in bacteria and an overlap coefficient of stannous are determined.

Turning to FIG. 4, the co-localization percentage of stannous within bacteria (of in situ plaque biofilm) is provided for three oral care products and a negative control. The procedures previously described are used. The biofilm is treated with the subject oral care compositions first, and then the treated biofilm is labeled with the bacterial and stannous probes. Using software, the pixel overlap of "green" bacterial probes and that of "red" stannous probes are identified, and then this value is divided by all non-black pixels (that include non-overlapping stannous probes) to provide a co-localization percentage of stannous in bacteria. FIG. 5 is a schematic of an illustrative example of how to determine how the co-localization percentage of stannous in bacteria (and an overlap coefficient discussed further below). The first step is determine a quantified overlap of stannous in bacteria by quantifying the overlap of measured fluorescence light from microbial fluorescent labeled cells and measured fluorescent light from stannous fluorescent labeled cells. Software is able to identify there are two red pixels (51a, 51b) indicative of the stannous probe outside of the bacterium (53) (but within the biofilm). Within the bacterium (53), there are seven green pixels (55a-55g) indicative of bacterial probes inside the bacterium (53). Three overlapping pixels (57a-57c) indicate stannous inside the bacterium (54). A quantified overlap of stannous in bacteria is identifying these overlapping pixels (57a-57c). In turn, the co-localization percentage of stannous within bacteria is determined by taking the three overlapping pixels and dividing by all the pixels in the biofilm (i.e., stannous probe and bacterial probe—located both inside and outside the bacteria). Said in another way, a step is taken to divide the quantified overlap of stannous in bacteria with all quantified measured fluorescent light (i.e., both from the bacterial probe and the stannous probe) in the biofilm to determine a co-localization percentage of stannous in bacteria. In FIG. 5, this value is 12. Therefore, the co-localization percentage stannous within bacteria in FIG. 5 is 25% (3/12). Generally the higher this percentage, the more efficacious the oral care product is in delivering stannous into bacteria.

Turning back to FIG. 4, three commercially available toothpaste products are: CREST® PRO-HEALTH™ (with 0.454 wt % Stannous fluoride) ("CPH"); SENSODYNE® COMPLETE PROTECTION (with 0.454 wt % Stannous fluoride) ("SSD"); CREST® CAVITY PROTECTION™ (0.243 wt % sodium fluoride) ("CCP") are assessed. Phosphate buffer solution ("PBS") is used as the negative control. The results show that CPH shows significantly higher co-localization percentage than SSD. This is consistent with both bactericidal efficacy comparison and plaque prevention efficacy in a clinical 4-day plaque result (unpublished).

Figure 6:
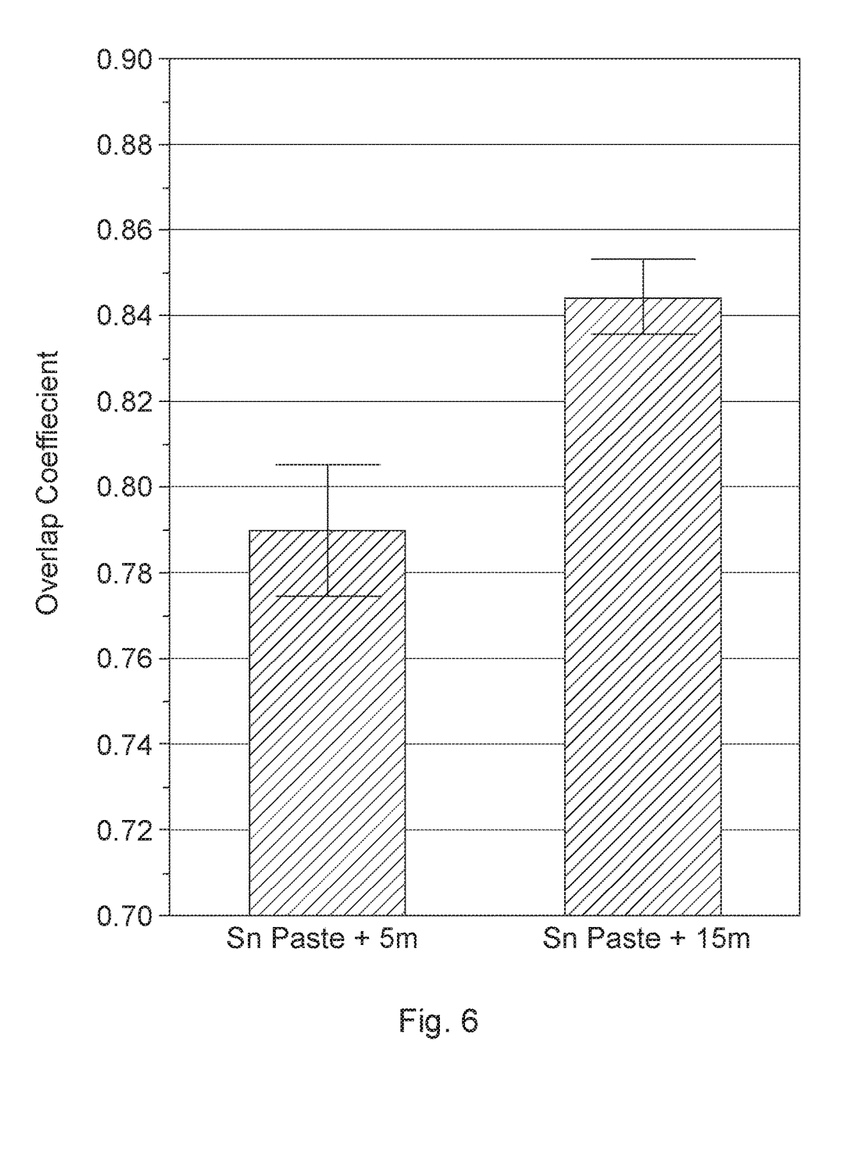
FIG. 6 is a bar graph providing an overlap coefficient of stannous containing paste on biofilm over time.

FIG. 6 looks at the effect of penetration time on an overlap coefficient of stannous when using the same stannous containing paste. The paste is left on the biofilm surface for 5 minutes ("5 m") and for 15 minutes ("15 m"). The 15 minute sample demonstrates a higher overlap coefficient (about 0.84) vs. the 5 minute sample (about 0.79) with $p<0.05$, indicating that the paste penetrates into deeper bacteria of the biofilm over time. To determine the overlap coefficient of stannous, the quantified overlap of stannous in bacteria is determined as described before. However, this value is divided with quantified measured fluorescent light from the stannous probe in the biofilm (as a whole). To better illustrate this point, reference is made to FIG. 5. The three overlapping pixels (57a-57c) indicate stannous inside the bacterium (54). A quantified overlap of stannous in bacteria is identifying these overlapping pixels (57a-57c). There are a total of five red pixels (i.e., two stannous pixels outside the bacterium (51a, 51b); and three stannous pixels inside the bacterium (57a-57c) (that are part of the overlapping pixels) are illustrative of the quantified measured fluorescent light from the stannous probe in the biofilm (as a whole). The quantified overlap of stannous in bacteria of three is divided by the quantified measured fluorescent light from the stannous probe in the biofilm of give to equal 0.6. This approach is used to provide the results of FIG. 6.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of quantitating sorption of stannous by microbial cells of a biofilm comprising the steps:
   a. wearing an oral appliance for 6 hours to 4 days wherein at least a portion of the oral appliance comprises hydroxylapatite (HA) as a surface for attachment of the biofilm;
   b. treating the biofilm with a stannous containing oral care product;
   c. labeling the biofilm with a microbial fluorescent probe;
   d. labeling the biofilm with a stannous fluorescent probe;
   e. providing excitation light to labeled biofilm;
   f. quantitating labeled cells by measuring fluorescence light emitted from the microbial labeled cells by confocal laser scanning microscopy (CLSM);
   g. measuring fluorescence light emitted from cells having labeled co-localized stannous ions by CLSM;
   h. quantitating co-localized stannous by quantifying the overlap of measured fluorescence light from microbial fluorescent labeled cells and measured fluorescent light from stannous fluorescent labeled cells;

wherein the portion of the oral appliance comprising HA further comprises a plurality of grooves, wherein an inside surface of the groove is said surface of the biofilm; and
   wherein at least one grove is about 250 microns to about 350 microns deep and from about 250 microns to about 350 microns wide.

2. The method of claim 1, wherein the steps of labeling the biofilm with the microbial fluorescent probe and the stannous fluorescent probe are before the step of treating the biofilm with the stannous containing oral care product.

3. The method of claim 1, wherein treating the in situ plaque biofilm with the stannous containing oral care product is treated in vivo.

4. The method of claim 1, wherein treating the in situ plaque biofilm with the stannous containing oral care product is treated ex vivo.

5. The method of claim 1, further comprising the step of having human subjects wear the oral appliance for 1-3 days wherein at least a portion of the oral appliance comprises hydroxylapatite (HA) as a surface for attachment of the biofilm wherein the HA is on the buccal side of the oral appliance.

6. The method of claim 1, wherein the biofilm is an in situ plaque biofilm.

7. The method of claim 1, wherein the HA surface of the biofilm is treated with the stannous containing oral care product ex vivo.

8. The method of claim 1, wherein the microbial fluorescent probe is a fluorescently labeled rRNA-directed oligonucleotide.

9. The method of claim 1, wherein the stannous fluorescent probe is selected from the group consisting of:
   a. tert-butyl (3',6'-diamino-3-oxospiro[isoindoline-1,9'-xanthen]-2-yl)carbamate;
   b. tert-butyl (3',6'-bis(dimethylamino)-3-oxospiro[isoindoline-1,9'-xanthen]-2-yl)carbamate;
   c. tert-butyl (3',6'-bis(diethylamino)-3-oxospiro[isoindoline-1,9'-xanthen]-2-yl)carbamate;
   d. tert-butyl (3',6'-bis(ethylamino)-2',7'-dimethyl-3-oxospiro[isoindoline-1,9'-xanthen]-2-yl)carbamate;
   e. tert-butyl (3',6'-diamino-2',7'-dimethyl-3-oxospiro[isoindoline-1,9'-xanthen]-2-yl)carbamate;
   f. tert-butyl (3-oxo-3',6'-di(pyrrolidin-1-yl)spiro[isoindoline-1,9'-xanthen]-2-yl)carbamate;
   g. tert-butyl (3-oxo-3',6'-bis(phenylamino)spiro[isoindoline-1,9'-xanthen]-2-yl)carbamate;
   h. tert-butyl (3-oxo-3',6'-di(piperidin-1-yl)spiro[isoindoline-1,9'-xanthen]-2-yl)carbamate;
   i. tert-butyl (3',6'-dimorpholino-3-oxospiro[isoindoline-1,9'-xanthen]-2-yl)carbamate;
   j. tert-butyl(2',7'-dibutyl-3',6'-bis(diethylamino)-3-oxospiro[isoindoline-1,9'-xanthen]-2-yl)carbamate;
   k. tert-butyl (2',7'-dimethyl-3-oxo-3',6'-di(piperidin-1-yl)spiro[isoindoline-1,9'-xanthen]-2-yl)carbamate;
   l. tert-butyl (3-oxo-1',2',3',4',10',11',12',13'-octahydrospiro[isoindoline-1,7'-pyrano[2,3-f:6,5-f]diquinolin]-2-yl)carbamate;
   m. tert-butyl (3-oxo-1',2',3',4',8',9',10',11'-octahydrospiro[isoindoline-1,6'-pyrano[3,2-g:5,6-g']diquinolin]-2-yl)carbamate;
   n. N-(3',6'-bis(diethylamino)-3-oxospiro[isoindoline-1,9'-xanthen]-2-yl)propionamide;
   o. N-(3',6'-bis(diethylamino)-3-oxospiro[isoindoline-1,9'-xanthen]-2-yl)butyramide; and
   p. N-(3',6'-bis(diethylamino)-3-oxospiro[isoindoline-1,9'-xanthen]-2-yl)pentanamide;

wherein emitted light of the stannous fluorescent probe is collected at a wavelength of 560-660 nm when the stannous fluorescent probe is exposed to excitation light at a wavelength of 543 nm.

10. The method of claim 1, further comprising the step of dividing said quantified overlap of stannous labeled bacteria with all quantified measured fluorescent light in the biofilm to determine a co-localization percentage of stannous in bacteria.

* * * * *